United States Patent [19]
Bani-Hashemi et al.

[11] Patent Number: 5,690,106
[45] Date of Patent: Nov. 25, 1997

[54] FLEXIBLE IMAGE REGISTRATION FOR ROTATIONAL ANGIOGRAPHY

[75] Inventors: Ali Reza Bani-Hashemi, Belle Mead; Sumitro Samaddar, Plainsboro, both of N.J.

[73] Assignee: Siemens Corporate Research, Inc., Princeton, N.J.

[21] Appl. No.: 491,325

[22] Filed: Jun. 30, 1995

[51] Int. Cl.$^6$ ............................................. A61B 6/00
[52] U.S. Cl. ................ 128/653.1; 382/130; 364/413.14; 364/413.19; 364/413.23; 128/654
[58] Field of Search ........................... 382/130; 378/62; 364/413.14, 413.23, 413.22, 413.19, 413.2; 128/653.1, 653.3, 653.4, 654

[56] References Cited

U.S. PATENT DOCUMENTS

| | | |
|---|---|---|
| 4,425,580 | 1/1984 | Haendle et al. |
| 4,450,478 | 5/1984 | Ledley |
| 4,516,261 | 5/1985 | Harding et al. |
| 4,551,800 | 11/1985 | Riederer et al. |
| 4,554,949 | 11/1985 | Kurihara |
| 4,559,557 | 12/1985 | Keyes et al. |
| 4,875,165 | 10/1989 | Fencil et al. |
| 4,885,688 | 12/1989 | Crawford |
| 5,031,620 | 7/1991 | Oe |
| 5,032,990 | 7/1991 | Eberhard et al. |
| 5,124,914 | 6/1992 | Grangeat |
| 5,148,499 | 9/1992 | Matsumura |
| 5,187,660 | 2/1993 | Civanlar et al. |
| 5,233,989 | 8/1993 | Honda |
| 5,241,471 | 8/1993 | Trousett et al. |
| 5,309,356 | 5/1994 | Nishide et al. |
| 5,412,563 | 5/1995 | Cline et al. |
| 5,481,653 | 1/1996 | Kashiwagi et al. |

OTHER PUBLICATIONS

"Editing Tools for 3D Medical Imaging", Ney et al., IEEE Computer Graphics & Applications, Nov. 1991, pp. 63–71.
"Flexible Mask Subtraction for Digital Angiography", Van Tran et al., IEEE Transactions on Medical Imaging, vol. 11, No. 3, Sep. 1992, pp. 407–415.

Primary Examiner—Marvin M. Lateef
Assistant Examiner—Shawna J. Shaw
Attorney, Agent, or Firm—Lawrence C. Edelman

[57] ABSTRACT

A digital subtraction angiography method useful for processing a mask and contrast series of two dimensional (2D) images acquired by rotational imaging of a selected volume of a body. The method reduces image artifacts caused by misregistration, and is unique in that for registration purposes it treats the acquired 2D images as a volume. The individual 2D images are stacked in a sequence so as to have the dimensions x, y and θ. A flexible volume registration is then performed to bring the mask and contrast volumes into a close match prior to subtraction.

18 Claims, 3 Drawing Sheets

CONTRAST SEQUENCE

MASK SEQUENCE

FLEXIBLE IMAGE REGISTRATION FOR ROTATIONAL ANGIOGRAPHY

BACKGROUND

1. Field of the Invention

The present invention relates to digital subtraction angiography (DSA), and more particularly, to the application of a flexible image registration technique to enable rotational DSA, wherein the mask and contrast image sequences are stacked and treated as volumes of data for performing flexible 3D image registration.

2. Background of the Invention

Digital subtraction angiography (DSA) is an imaging technique useful for visualizing blood vessels inside the body of a patient. A contrast medium bolus which is substantially opaque to X-rays is injected into the vessels and an X-ray image known as a contrast image is acquired by an x-ray imaging system. Another image called the mask is acquired prior to the injection of the contrast medium and a difference image is obtained by subtracting the mask image from the contrast image. Under ideal conditions, nothing appears in the subtracted image except the blood vessels of the patient. Typically, however, two types of motion cause artifacts to appear. One type is global motion between the patient and the imaging system. The other type is local motion of the soft tissue that occurs between the acquisition time of the two images. Various techniques have been developed recently for solving the motion artifact problems in DSA. These techniques fall within the topics of motion correction and image registration.

Additionally, there are reasons other than motion which cause the artifacts in the subtracted image. One is fluctuations of the intensity of the X-ray source between the two acquisitions. Another is the scattering effects of the contrast medium. The present invention is only directed to motion related artifacts.

Figure 1:
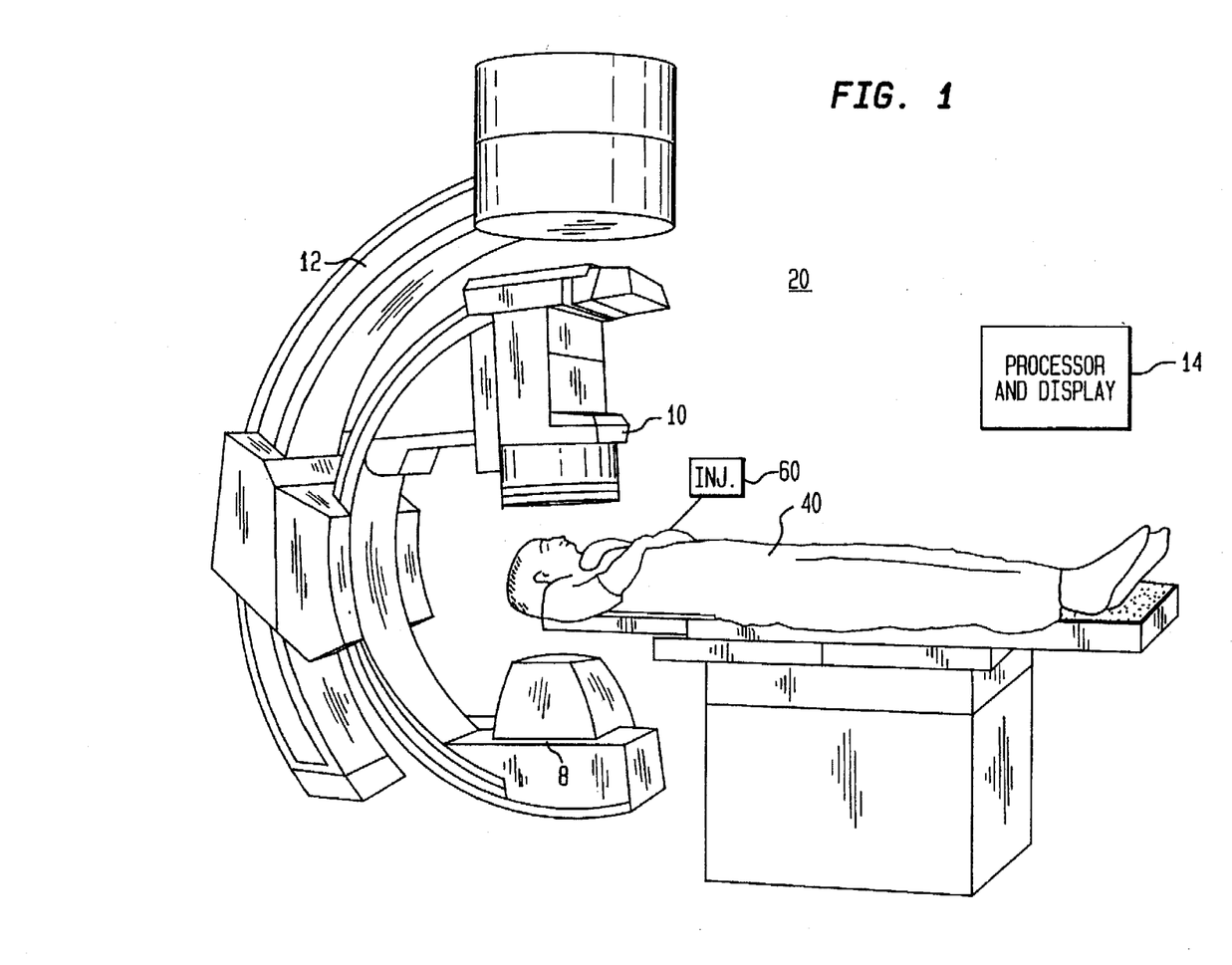
FIG. 1 is a schematic illustration of an imaging system constructed in accordance with an embodiment of the present invention.
Figure 2:
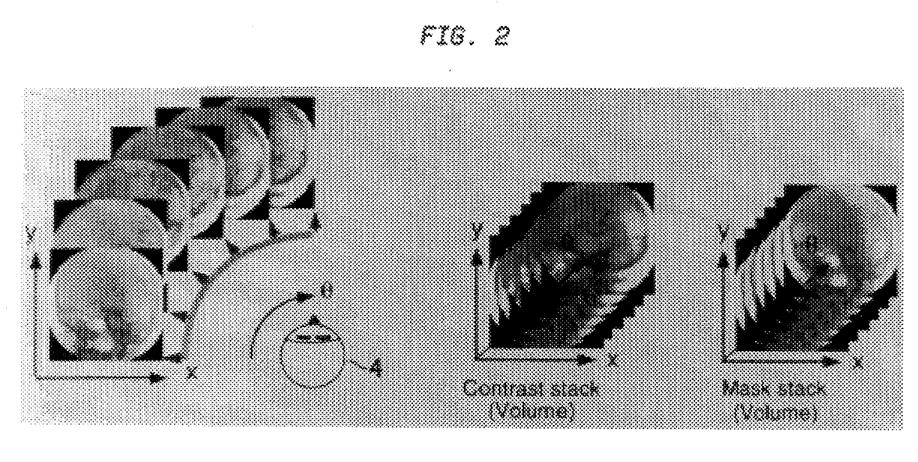
FIG. 2 is a graphical illustration useful for understanding the process of acquiring rotational angio sequences and forming stacks of 2D image data using a rotational digital angiography imaging apparatus.

Rotational angiography is a relatively new technique in which, as shown in FIG. 1, an X-ray imaging system 20 rotates about a patient 40 while an injector 60 injects a contrast medium into the blood vessels of the patient. An X-ray source 8 and image intensifier/camera imaging system 10 are carried by a C-arm 12 which controllable positions the projection of X-ray radiation through the patient. Processing of the image data acquired by camera 10 in a processor/display system 14 results in a sequence of angio images that, when played back in a cine fashion, gives a 3D spatial effect. FIG. 2 graphically illustrates this process.

The notion of DSA can be applied to rotational angiography as well. To applicant's knowledge, this technique was first demonstrated at the 1992 Radiological Society of North America (RSNA) show held in Chicago, and since then has gained much attention. In rotational DSA, as in rotational angiography noted above, two runs are made: one without vessel opacification (the mask run) and the other with opacification (the contrast run). As shown in FIG. 2, the C-arm carries the X-ray source and camera in an arc about the patient at an angular speed of a few degrees per second for older angio machines, and up to 30 degrees per second for the latest models. The rate of X-ray firing varies from a few times per second (typically 6) to as high as 15 times per second, with an image generated for each firing.

Once the end of the mask run is reached, the injection of a contrast bolus is started by the injector and the C-arm reverses its motion and moves in the opposite direction. The X-ray firing continues and the contrast run series of images are acquired. Ideally, one would like to have identical angles for corresponding images in the mask and contrast runs. However, due to inaccuracies of the C-arm mechanism, mask and contrast run images are often taken at slightly different angular positions. An imaging study typically takes on the order of 10 to 20 seconds. During this time the patient invariably has some motion.

As previously noted, there are a number of reasons for motion artifacts to appear in the resulting DSA sequence. The main sources for the artifacts are:

1. Corresponding mask and contrast images do not correspond to the same angles, due to nonrepeatability and inaccuracy of the C-arm.
2. Corresponding mask and contrast images do not correspond to the same position of the C-arm, due to its mechanical instability. This is equivalent to global patient motion, the components of which are translation and rotation of the acquired images.
3. Local patient motion due to muscle contraction, breathing, gas (in the abdominal studies), etc.

These sources exclude the fluctuations of the X-ray intensity between the two runs. The effect of global motion on image magnification is also excluded (i.e., change in the relative distance between the X-ray imaging system and the subject).

Let us now consider what the resulting artifacts will be for each of the mentioned sources. Let us first consider the nonrepeatability of the C-arm, which results in taking the corresponding mask and contrast images at slightly different angles. This causes misregistration, which in turn results in residual artifacts in the DSA images. Suppose that a contrast image was acquired at angular position $\theta$ and the corresponding mask image was taken at position $\theta+\delta\theta$. To get a perfect subtraction, one would need the mask image at position $\theta$. The question is, how different are the two mask images taken at angles $\theta$ and $\theta+\delta\theta$? The answer is that a transformation which would map one mask image to another is a not an affine transformation; rather, it is a complicated warping which depends on the object.

The effect of global motion is a global translation and rotation in the image which causes residual artifacts. To correct these artifacts one needs to translate and rotate the mask image to minimize the artifacts in the subtraction image.

Local motion due to breathing, for example, results in local deformations. Correction requires local deformation of the mask to minimize artifacts.

Several researchers have attempted eliminating these types of artifacts. Geometric transformations have been used in digital subtraction angiography to transform the mask image prior to subtraction. The most common of these transformations is 2D translation used for reducing patient motion. Introducing rotation in the geometric transformation makes sense only if the rotation is about an axis perpendicular to the image plane.

Rubber sheet masking for deforming the mask image prior to subtraction has also been tried, see THE REDUCTION OF MOTION ARTIFACTS IN DIGITAL SUBTRACTION ANGIOGRAPHY BY GEOMETRICAL IMAGE TRANSFORMATION by Fitzpatrick et al. published in SPIE Medical Imaging, Vol. 914, pages 379–386, 1988. Many techniques based on global warping use a global measure-of-goodness for the quality of subtracted image. Deterministic Sign Change (DSC) criterion, first suggested in A NEW CLASS OF SIMILARITY MEASURES FOR ROBUST IMAGE REGISTRATION by Venot et al. published in Computer Vision, Graphics, Image Processing, 28:176–184, March 1984, seems to be a generally accepted measure of quality for DSA. FAST RUBBER SHEET MASKING FOR DIGITAL SUBTRACTION ANGIOGRAPHY by Zuiderveld et al. published in SPIE Medical Imaging, Vol. 1137, pages 22–30, 1989, point out the dependency of DSC criterion on image statistics. In addition, since image statistics vary largely with image position, a global DSC criterion cannot represent the quality of the subtracted image. Van Tran et al (in an article entitled FLEXIBLE MASK SUBTRACTION FOR DIGITAL ANGIOGRAPHY published in IEEE Transactions on Medical Imaging, 11(3):407–415, September 1992) and Zuiderveld et al. deal with this problem by breaking the mask image into many small 2D sub-images, and computing a transformation that optimizes the DSC criterion for each sub-image.

It would be desirable to provide a method and apparatus which would improve the quality of the vascular images produced using rotational imaging techniques.

It would also be desirable that the improvement result by an automatic, rather than semi-automatic or manual processing of the acquired image data.

Additionally, it would be desirable to find a way to use DSA techniques in a rotational imaging system.

SUMMARY OF THE INVENTION

A digital subtraction angiography method useful for processing a mask and contrast series of two dimensional (2D) images acquired by rotational imaging of a selected volume of a body. The method reduces image artifacts caused by misregistration, and is unique in that for registration purposes it treats the acquired 2D image data as a volume. The individual 2D images are stacked in a sequence so as to have the dimensions x, y and $\theta$. A flexible volume registration is then performed to bring the mask and contrast 2D images into a close match prior to subtraction.

More specifically, the method comprises the following steps. Acquiring first and second volumes of 2D data sets representative of rotationally offset images of substantially the same selected volume in the body, the first and second data sets being acquired at different times corresponding to a pre- and a post, respectively, application of a process to the body to differentially affect imaging characteristics of the selected volume. Determining common reference points for spatially corresponding sub-areas in the data sets. Comparing in a 3D spatial manner data in sub-areas of the second data set with data in corresponding sub-areas in the first data set in order to determine a new reference point in each of the sub-areas of the first data set which results in a best match of the spatial similarity of the data in a corresponding sub-area of the second data set. Spatially interpolating new data for the sub-areas of the first data set using the new reference points determined above and the originally acquired data of the first data set, thereby generating a new first data set for the volume. Subtracting the new first data set from the second data set, for generating a subtraction data set representative of a series of 2D images of the selected volume in which the given portion is accentuated.

These advantages as well as other features of the present invention will be apparent from the description of the preferred embodiment of the invention and the claims.

For a fuller understanding of the present invention, reference should now be made to the following detailed description and the accompanying drawings.

DETAILED DESCRIPTION OF THE PREFERRED EMBODIMENTS

As was described in the background portion of this specification, a major source of artifacts in the subtraction image obtained by rotational imaging results from the inaccuracy and nonrepeatability of the C-arm. As shown in FIGS. 1 and 2, the data acquisition process comprises two runs, one without vessel opacification (mask run) and the other with opacification (contrast run). The C-arm 12 carries the X-ray source 8 and camera 10 in a circle about the patient 40. Once the end of the mask run is reached, the injection of the contrast bolus by injector 60 is started and the C-arm reverses its motion and moves in the opposite direction. The firing of X-ray source continues and a series of images known as the contrast run are acquired.

Ideally, one would like to have identical angles for corresponding images in the mask and contrast runs. However, due to the inaccuracy and nonrepeatability of the C-arm mechanism, mask and contrast images are taken at different angular positions. If the mask image was acquired at angular position $\theta$ and the corresponding contrast image was taken at position $\theta+\delta\theta$. To get a perfect subtraction, we would need the mask image at position $\theta+\delta\theta$.

X-ray image is a radiographic projection of an object onto a plane. It may be considered as a two dimensional function of x and y such that at each point (x, y) it records the aggregate of all the absorptions along the ray emanating from the X-ray source to the point (x, y) on the image plane.

Suppose that a series of images are taken by going around the subject. This creates a three dimensional volume which is a function of x, y, and $\theta$. In X-ray imagery, unlike reflective imagery (i.e., conventional photography), occlusion does not create discontinuity in this three dimensional function (volume). For this reason, two X-ray images taken from slightly different angles have high degree of correlation. Suppose that two mask images were taken at angles $\theta_1$ and $\theta_2$, and it is desired to have mask image at angular position $\theta_1+\delta\theta$, where $\delta\theta<|\theta_2-\theta_1|$. High degrees of correlation between mask images at angular positions $\theta_1$ and $\theta_2$ implies that the mask image at position $\theta_1+\delta\theta$ may be computed by linear interpolation of the two images at angles $\theta_1$ and $\theta_2$.

This kind of interpolation is embedded in the three dimensional flexible registration method of the present invention. The flexible registration has other components, such as; scaling, rotation, and translation along x and y dimensions. These components remedy artifacts caused by patient motion. However, the artifacts caused by the C-arm inaccuracy are most effectively dealt with by interpolation along $\theta$ dimension.

Please note that although an x-ray system is used for illustrative purposes, it should be clear that the invention is applicable to registration of a series of 2D images obtained by imaging apparatus using other technologies, such as magnetic resonance, positron emission, etc.

For describing the present method, it is best to start with description of a three dimensional flexible registration technique developed by the present inventors for Digital Subtraction Computed Tomography Angiography CT DSA, which tolerated nonrigid misregistration, as well as, intensity variations between the mask and contrast volumes. That technique was inspired by, and improves upon a two-dimensional technique first introduced by Van Tran et al (as described in the forenoted Van Tran article), to suppress artifacts caused by motion and gray level variations in regular (i.e., single pose) coronary DSA. In that technique, the contrast volume is subdivided into N non-overlapping small 2D sub-volumes, each identified by $B^n$. The center of each sub-volume is identified by a point $p^n$. A transformation $W^n$ is computed that maps each $B^n$ into a similar sub-volume on the mask volume. This transformation is computed based on the following matching criterion. Letting each point of the sub-volume $B^n$ be referred to as $p_m{}^n$ and the corresponding mapped point on the mask volume as $q_m{}^n$, for each sub-volume $B^n$ a difference volume is computed by subtracting the the intensity at each $q_m{}^n$ in the mask volume from the intensity at $p_m{}^n$ in the contrast volume. This is shown in volume. This is shown in the following equation.

$$D_{ssc}{}^n(p_m{}^n) = C(p_m{}^n) - M(q_m{}^n) \qquad [1]$$

where $q_m{}^n = (q_{mx}{}^n, q_{my}{}^n, q_{mz}{}^n)$ is formed by mapping $p_m{}^n = (p_{mx}{}^n, p_{my}{}^n, p_{mz}{}^n)$ using transformation $W^n$. The transformation $W^n$ is in turn composed of the three transformations; scaling, rotation, and translation. $W^n$ is a homogeneous transformation matrix represented by equation 2.

$$W^n = \begin{bmatrix} 1 & 0 & 0 & t_x{}^n \\ 0 & 1 & 0 & t_y{}^n \\ 0 & 0 & 1 & t_z{}^n \\ 0 & 0 & 0 & 1 \end{bmatrix} \begin{bmatrix} r_{11}^n & r_{12}^n & r_{13}^n & 0 \\ r_{21}^n & r_{22}^n & r_{23}^n & 0 \\ r_{31}^n & r_{32}^n & r_{33}^n & 0 \\ 0 & 0 & 0 & 1 \end{bmatrix} \begin{bmatrix} s_x{}^n & 0 & 0 & 0 \\ 0 & s_y{}^n & 0 & 0 \\ 0 & 0 & s_z{}^n & 0 \\ 0 & 0 & 0 & 1 \end{bmatrix} \qquad [2]$$

The mapping from $p_m{}^n$ in the contrast volume to $q_m{}^n$ in the mask volume is based on the following homogeneous transformation.

$$\begin{bmatrix} q_{mx}^n \\ q_{my}^n \\ q_{mz}^n \\ 1 \end{bmatrix} = \begin{bmatrix} 1 & 0 & 0 & t_x{}^n \\ 0 & 1 & 0 & t_y{}^n \\ 0 & 0 & 1 & t_z{}^n \\ 0 & 0 & 0 & 1 \end{bmatrix} \begin{bmatrix} r_{11}^n & r_{12}^n & r_{13}^n & 0 \\ r_{21}^n & r_{22}^n & r_{23}^n & 0 \\ r_{31}^n & r_{32}^n & r_{33}^n & 0 \\ 0 & 0 & 0 & 1 \end{bmatrix} \begin{bmatrix} s_x{}^n & 0 & 0 & 0 \\ 0 & s_y{}^n & 0 & 0 \\ 0 & 0 & s_z{}^n & 0 \\ 0 & 0 & 0 & 1 \end{bmatrix} \begin{bmatrix} p_{mx}^n \\ p_{my}^n \\ p_{mz}^n \\ 1 \end{bmatrix} \qquad [3]$$

$D_{ssc}{}^n$ in equation 1 is the subtraction sub-volume. If the corresponding sub-volume in the contrast and the mask are perfectly aligned, the subtraction sub-volume $D_{ssc}$ is just the superposition of noises. If this super-positional noise is symmetrically distributed about zero, the statistically best registration coefficients correspond to the maximum number of sign changes is $D_{ssc}{}^n$.

When the noise levels are low, the subtraction sub-volume $D_{ssc}{}^n$ in equation 1 becomes null. A deterministic sign change (DSC) criterion is then applied. In order to produce a fixed pattern of sign changes, a fixed value K, determined by image statistics, is periodically added to or subtracted from the subtraction sub-volume $D_{ssc}{}^n$, $$D^n_{dsc} = D^n_{ssc} + (-1)^{i+j+k} K \qquad [4]$$

In equation 4, i, j, k are the indices for each voxel within sub-volume $B^n$. The number of sign changes is then computed, and the selected registration coefficient corresponds to the maximum number of sign changes in $D_{dsc}{}^n$ So, the Best-Match-Criterion (BMC) is the maximum of the deterministic sign changes in the difference sub-volume.

In the present invention, our forenoted three-dimensional flexible registration technique is adapted for use to provide registration for a series of 2D images acquired by rotational imaging. In accordance with the principles of the invention, the volume being registered is a stack of 2D X-ray images acquired over different angles at different times. The sub-portions of the flexible 3D registration are no longer cubes. Rather, they are sub-portions of the 2D X-ray images that can be placed at any point on the θ axis.

In the remaining description, the data used by the inventive method will be referred to as a volume, while keeping in mind that it is actually a stack of 2D image data.

GENERAL DESCRIPTION OF THE METHOD

The flexible registration method starts by automatically selecting a set of uniformly distributed control points within each contrast slice. For each control point a neighborhood in the form of a sub-block is selected. This sub-block is used as a matching window. A similar sub-block around the same coordinates in the corresponding mask image is selected. Deterministic-Sign-Change is used as the Best-Match-Criterion (BMC), to determine a transformation consisting of scaling along two directions (x and y), in-plane rotation (about the θ axis), and translation along three (x, y, and θ) axes. It should be noted that out-of-plane rotation (i.e., about the x and y axes) has been eliminated, because it does not make any physical sense. Subdividing the data into small two dimensional blocks instead of three dimensional sub-volumes also makes physical sense, because selecting more that one slice along θ and scaling along θ are physically meaningless.

Figure 3:
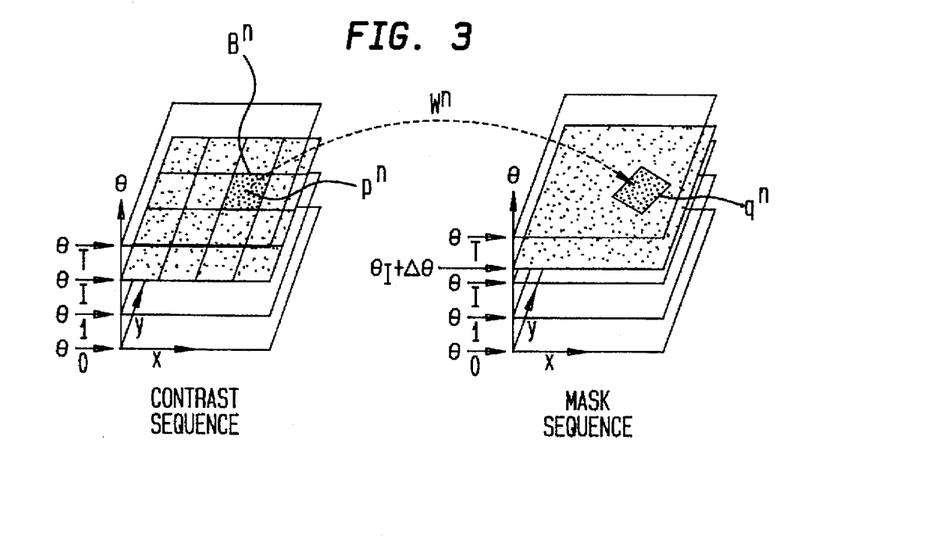
FIG. 3 is a graphical illustration useful for understanding the flexible registration technique of the present invention.
Figure 4:
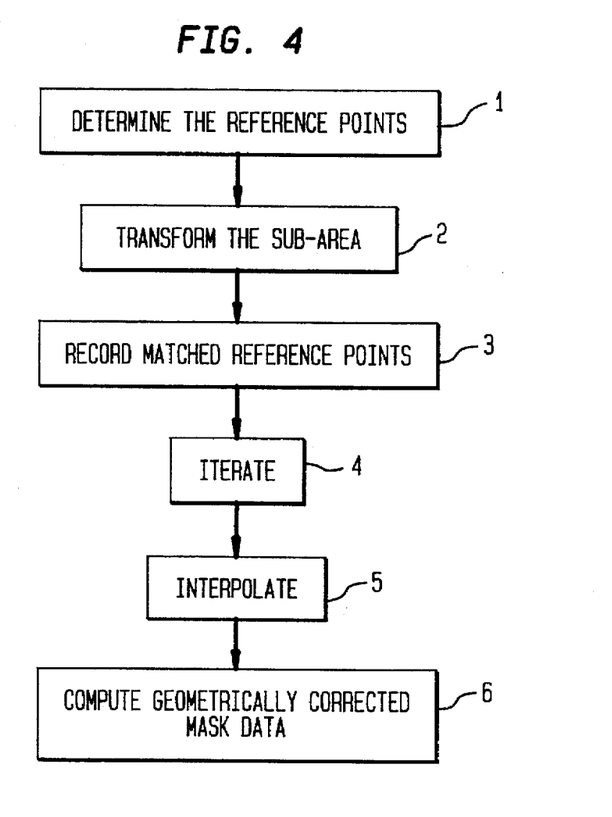
FIG. 4 is a flow chart of the flexible registration technique of the present invention.

FIG. 3 shows the method of the invention. There are six parameters controlling the best match criterion, which is the deterministic-sign-change (DSC). These parameters consist of scaling along x, scaling along y, rotation about θ axis, and translation along all three axes (x, y, and θ). Translating the sub-block between slices along θ means interpolating between neighboring slices.

The method starts with selecting a number of control points in each image slice. These points are selected in an organized pattern (e.g., one every 16 pixels). A sub-block is selected centered around every control point. This sub-block is then used as a search window. The size of the block is selected empirically. The problem of matching the contrast data with the mask data is that the two data sets are not identical; the contrast data has the presence of the contrast image medium. The matching must handle the similarity determination based on the background information. Therefore, the search window must be large enough not to be covered by vessels, yet it must contain enough of the background for determining the similarity measure. The flexible registration is realized by breaking the image data into a number of rigid areas that are free to move independently from each other. Small search windows result in better approximation of flexible registration. So, there is a tradeoff between keeping the search window large in order to get more accurate matching criterion and realizing flexible registration.

Let us refer to each control point (center of each area) by $p^n$. Similar to our previous 3D flexible registration, a transformation $W^n$ is computed that maps a two dimensional area $B^n$ to a similar area on the mask data set.

The transformation $W^n$ is composed of three transformations; scaling, rotation, and translation. $W^n$ is a homogeneous transformation matrix represented by equation 5.

$$W^n = \begin{bmatrix} 1 & 0 & 0 & t_x^n \\ 0 & 1 & 0 & t_y^n \\ 0 & 0 & 1 & t_\theta^n \\ 0 & 0 & 0 & 1 \end{bmatrix} \begin{bmatrix} \cos\phi & \sin\phi & 0 & 0 \\ -\sin\phi & \cos\phi & 0 & 0 \\ 0 & 0 & 1 & 0 \\ 0 & 0 & 0 & 1 \end{bmatrix} \begin{bmatrix} s_x^n & 0 & 0 & 0 \\ 0 & s_y^n & 0 & 0 \\ 0 & 0 & 1 & 0 \\ 0 & 0 & 0 & 1 \end{bmatrix} \quad [5]$$

The mapping from the $p_m^n$ in the contrast data to $q_m^n$ in the mask based on the following homogeneous transformation.

$$\begin{bmatrix} q_{mx}^n \\ q_{my}^n \\ q_{m\theta}^n \\ 1 \end{bmatrix} = \begin{bmatrix} 1 & 0 & 0 & t_x^n \\ 0 & 1 & 0 & t_y^n \\ 0 & 0 & 1 & t_\theta^n \\ 0 & 0 & 0 & 1 \end{bmatrix} \begin{bmatrix} \cos\phi & \sin\phi & 0 & 0 \\ -\sin\phi & \cos\phi & 0 & 0 \\ 0 & 0 & 1 & 0 \\ 0 & 0 & 0 & 1 \end{bmatrix} \begin{bmatrix} s_x^n & 0 & 0 & 0 \\ 0 & s_y^n & 0 & 0 \\ 0 & 0 & 1 & 0 \\ 0 & 0 & 0 & 1 \end{bmatrix} \begin{bmatrix} p_{mx}^n \\ p_{my}^n \\ p_{m\theta}^n \\ 1 \end{bmatrix} \quad [6]$$

Note that in the direction of $\theta$ there are only a limited number of images stacked up (typically 50 images). Translation along $\theta$ may be done in fractions of the slice distance. In this case tri-linear interpolation is performed to compute the in-between sub-area.

FLOW CHART

As noted above, the present method comprises a warping that transforms the mask image to a best-match of the contrast image. As previously discussed, the mask data will not exactly match the contrast data for a number of reasons. Most importantly, corresponding regions will not match due to presence of vessels in the contrast data. As well known, it is this phenomena that is relied on to produce the images of interest in DSA. In addition, the contrast and mask images will have different intensities due to X-ray intensity fluctuates from one scan to the other. This makes it difficult to measure similarities between corresponding regions.

Using the gradient of the mask and contrast images (instead of the raw intensities) overcomes some of these problems. By using the gradient images, the extent of blood vessels in the contrast is now reduced to only the boundary of the vessels since the gradient inside the vessel is nearly zero. Thus, registration is done using image gradients. The transformations, in this case, are all computed based on the gradient images. The subtraction is, of course, computed using the raw intensity data.

In conjunction with the following description, the reader should now refer to FIG. 3, which illustrates a flow chart of the flexible 2D registration technique of the present invention.

Step 1) Determine the Reference Points

These points are chosen every P point along the two axes of the (gradient of) contrast images, forming a three dimensional array of points. The number P is determined by the user and specifies the distance between reference points. The choice of P is purely empirical. In our experiments P was chosen to be 16. For each reference control point, a match sub-area with size B is selected, with the reference point at the center. This sub-area is used as a search window to find the best match.

Step 2) Transform the Sub-Area

A function of the difference between the contrast and mask sub-areas is the error function that needs to be minimized to obtain the best match. This function minimization is carried out using, for example, the "direction set method" described by R. P. Brent in his book entitled *Algorithms for Minimization Without Derivatives*, published by Prentice-Hall, Englewood Cliffs, N.J. 1973. Brent's direction set method uses conjugate directions and yields an optimum transformation. This method is a form of "gradient descent algorithm" and is described in greater detail later on along with a description of the BMC.

Step 3) Record Matched Reference Point

Record the center of the match sub-area after the BMC is achieved. This would provide the best local translation, rotation, and scaling that would bring the reference point in the mask to register with the reference point in the contrast data.

Step 4) Iterate

Repeat the process, starting from Step 2), for each reference point.

Step 5) Interpolate

The translation, rotation, and scaling computed for each reference point determines the transformation that must be applied to bring the reference points into registration. The points falling in between the reference points must have transformations as well. Linear interpolation is applied based on neighboring reference points to compute the transformation for each non-reference point. The interpolation is based on six-component vector fields. Note that for each 3D point a six component vector represents the transformation, hence, a 3D field.

Step 6) Compute Geometrically Corrected Mask data

Use the mapping computed in Step 5) to compute the geometrically corrected mask data and subtract it from the contrast data.

BEST MATCHING CRITERION (BMC)

The choice of BMC is of utmost importance in this matching process. In conventional image registration simple correlation techniques are used, most common of which is sum of absolute values of differences}. A problem is that small number of large differences (caused by misregistration of bright voxels) can effect the sum disproportionately. Moreover, these methods work correctly only when the features of interest that are to be compared are nearly identical. This is not the case in DSA, since vessels are present in the contrast data and they are absent in the mask data. The criterion for matching must be clever enough to only include the underlying features and exclude the differences caused by the vessels.

A class of similarity measures based on nonparametric statistical consideration is known which improves the registration performance over conventional methods such as the correlation function, see A. Venot et al, "A New Class of Similarity Measures for Robust Image Registration", published in *Computer Vision, Graphics, Image Processing*, 28:176–184, March 1984. When the noise level in the image is greater than the digitization precision, the stochastic sign-change (SSC) criterion is applied by first taking difference of contrast and mask images.

Refer to intensity of the points $p_i^n$ in the contrast data set within the search window $B^n$ by $I_c(p_i^n)$. Similarly, $I_m(q_i^n)$ is intensity of the point $q_i^n$ in the mask data set. $q_i^n$ is the mapping of $p_i^n$ by the transformation $W^n$. A difference subimage $D^n_{ssc}$ is computed using equation 7.

$$D_{ssc}^n(p_i^n) = I_c(p_i^n) - I_m(q_i^n) \quad [7]$$

If $I_c$ and $I_m$ are perfectly aligned, the subtraction image $D_{ssc}$ is just the superposition of noises from $I_c$ and $I_m$. If this superpositional noise is symmetrically distributed about zero, the statistically best registration coefficients correspond to the maximum number of sign-changes is $D_{ssc}$.

When the noise levels are low, the subtraction image $D_{ssc}$ in equation 1 becomes null. A deterministic sign-change (DSC) criterion is then applied. In order to produce a fixed pattern of sign-changes, a fixed value K, determined by image statistics, is periodically added to or subtracted from the subtraction image $D_{ssc}$. A new difference subimage $D_{dsc}^n$ is computed using equation 8.

$$D^{ndsc} = I_c(p_i^n) - I_m(q_i^n) + (-1)^{i+j}K \quad [8]$$

In this equation the constant K depends on the image statistics. The term $(-1)^{i+j}K$ introduces a checkerboard-board pattern that is added to the difference image. As discussed earlier, if the noise variance is large, then the maximum number of sign-changes in the subtraction image indicates the best match. However, if the noise level is too low, then there will not be sufficient number sign-changes for a good judgement about the quality of the match. In this case the deterministic pattern $(-1)^{i+j}K$ gets added to the image resulting in a number of sign-changes that would be maximum for the best match.

The choice of K depends on image statistics. One would like to keep K as low as possible. Considering discrete (quantized) image intensity representation, one would want to keep K as low as 1. However, the two contrast and mask data sets have different intensity floors due to intensity fluctuations of the X-ray, as well as, the scatter effects caused by the contrast medium. There might be other reasons that the mask and contrast image will have different intensity floors, however, discussion about these reasons are beyond the scope of this specification. It suffices to mention that these variations result in an offset in the subtraction result. This offset is present even in the background regions where the contrast and mask are supposed to be identical. The optimum choice for K is equal to the amount of the offset. This guarantees a maximum number of sign-changes for the best match. It is important to note that increasing K beyond its optimum level increases the number of sign-changes, however, that increase does not correspond to better quality of match. In our experiments K has been set to be around 6.

In our preferred embodiment of the method we have used the DSC approach of BMC. Gradient images (instead of intensity images) are used to find the best match. From experiments, it was concluded that the use of gradient image improves the quality of match. If, however, intensity images are to be used for matching, the following modification showed to have more success. We modified the basic DSC criterion to exclude from computation those pixels where the sign of the difference corresponds to vessels. In the computation of DSC we only use, the difference values that are positive. A good portion of the negative values in the difference image are assumed to be caused by vessels, that appear to be dark in the contrast images. This modified method of computing DSC is superior to the traditional correlation techniques, such as, sum of absolute differences. This has been confirmed experimentally.

Recently a new technique known as Coincident Bit Counting (CBC) has been presented that is supposed to perform better in cases where noise if not distributed symmetrically about zero. We did not see a need for CBC technique.

DIRECTION SET METHOD IN MULTIDIMENSIONS

A true "gradient descent method" requires the computation of the gradient of the BMC. Usually BMC is maximized for best match, whereas gradient descent algorithms minimize some function. Hence, we use the negative values of BMC for minimization. Since, the BMC is a function of 6 variables (i.e., 3 translations, one rotation and two scalings), the computation of gradient is expensive. It would be computationally more effective if the function minimization could be carried out as a sequence of one-dimensional minimizations along conjugate or non-interfering directions such that minimization along one direction is not spoiled by subsequent minimization along another.

All direction set methods consist of prescriptions for starting with some arbitrary set of directions, typically unit vectors along each dimension. These methods then sequentially perform function minimization along each direction in the direction set. At the end of each iteration, this set of directions is updated, so that the direction set ultimately approaches the property of conjugate directions.

Brent's version of the direction set method is probably the best known. After minimizing along each dimension, this method adds the direction corresponding to the net motion in multidimensional space to the direction set. This, after all is the average direction moved after trying all possible directions in the direction set. For a valley whose long direction is twisting slowly, this direction is likely to give us a good run along the new long direction. Simultaneously, the method drops the direction along which the function made its largest decrease from the direction set. This seems paradoxical, since that direction was the best of the previous iteration. However, it is also likely to be a major component of the new direction that we are adding, so dropping it gives us the best chance of avoiding a buildup of linear dependence. Remember, we are trying to construct a set of directions which are linearly independent and mutually conjugate.

The computational complexity of the direction set method of function minimization depends on the number of dimensions on which minimization is carried out. The total degree of freedom for our registration problem is six, with three translations, two scalings and one rotation in the plane of projection. The described implementation allows the user to perform minimization only along certain dimensions if some a priori information about the nature of data is known. Thus, faster registration can be performed by varying only the translation parameters and holding the rotation and scaling parameters constant, usually to zero rotation and unity scaling. Scaling transformations are usually needed to account for organs such as heart, rib cage during breathing, etc. They are usually not necessary for head, neck, or abdominal studies. Rotation components can be subsumed by translation if we use a finer spacing of reference points and/or smaller search match window. The user is also allowed to specify the accuracy of each one-dimensional minimization. This is controlled by a parameter that specifies the smallest decrease in function value necessary to continue the minimization in a direction.

HIERARCHICAL REGISTRATION

Great computational advantage can been obtained by initially carrying out a coarse registration using fewer reference points with larger match subvolumes which were subsampled for the purpose of evaluating the BMC. Finer registration can be then performed by using a finer distribution of reference points with smaller match subvolumes with lesser (or no) subsampling and for fewer directions, for example only for translation.

Thus, there has been shown and described a novel image registration technique for rotational DSA which satisfies all the objects and advantages sought therefore. Many changes, modifications, variations and other uses and applications of the subject invention will, however, become apparent to those skilled in the art after considering this specification and its accompanying drawings, which disclose preferred embodiments thereof. For example, as previously noted, the registration technique can be useful in imaging systems using various other techniques, such as magnetic resonance, positron emission, etc. All such changes, modifications, variations and other uses and applications which do not depart from the spirit and scope of the invention are deemed to be covered by this patent, which is limited only by the claims which follow as interpreted in light of the foregoing description.

What we claim is:

1. A digital subtraction angiography method useful for rotational 2D imaging of a selected volume of a body, comprising the following steps:

acquiring first and second volumes of 2D data sets representative of a series of rotationally offset 2D images of substantially the same selected volume in the body, the first and second data sets being acquired at different times corresponding to a pre- and a post, respectively, application of a process to the body to differentially affect imaging characteristics of the selected volume;

determining common reference points for spatially corresponding sub-areas in each image of the series of rotationally offset 2D images in the first and second data sets;

comparing in a 3D spatial manner data in sub-areas of the second data set with data in corresponding sub-areas in at least two of the rotationally offset 2D images of the first data set in order to determine a new reference point in each of the sub-areas of the first data set which results in a best match of the spatial similarity of the data in a corresponding sub-area of the second data set;

spatially interpolating new data for sub-areas of the first data set using the new reference points determined above and the originally acquired data of the first data set, thereby generating a new first data set for the selected volume; and subtracting the new first data set from the second data set, thereby generating a subtraction data set representative of a series of 2D images of the selected volume in which the given portion is accentuated.

2. The method of claim 1, comprising the further step of applying said subtracted data set to a display device for displaying an image on said display device of said selected volume wherein said given portion is accentuated.

3. The method of claim 1, wherein said comparing step comprises 3D transformation of the spatial positioning of the data in said first data set before performing said comparing.

4. The method of claim 1, wherein said acquiring step includes a processing step for developing a gradient function of the data in said first and second data sets, and said comparing step comprises 3D transformation of the spatial positioning of the gradient function of the data in said first data set and comparing with the result of the gradient function applied to the data in said second data set.

5. The method of claim 3, wherein said 3D transformation step comprises 3D translation, 2D rotation, and 2D scaling in discreet fractional steps of the spatial positioning of the data in said first data set.

6. The method of claim 5, wherein said spatial interpolating step comprises tri-linear interpolation.

7. The method of claim 1, wherein said determining and comparing steps are iteratively repeated until a best match criterion is satisfied, and then said new reference point is determined.

8. The method of claim 7, wherein said best match criterion comprises a maximization of a stochastic-sign-change function.

9. The method of claim 7, wherein said best match criterion comprises a maximization of a deterministic-sign-change function.

10. The method of claim 7, wherein said best match criterion comprises a minimization of the sum of squared differences.

11. The method of claim 7, wherein said best match criterion comprises a minimization of the sum of absolute differences.

12. The method of claim 9, wherein a checkerboard pattern is added to the result of said comparing step before evaluation of the deterministic-sign-change function.

13. The method of claim 1, wherein said acquiring step comprises exposing said selected volume to x-ray beams before and after injection of an x-ray contrast agent into blood vessels of said body, and determining respective first and second data sets of intensity values representative of a series of sequential images of said patient through said selected volume.

14. A digital subtraction angiography apparatus adapted for rotational 2D imaging of a selected volume of a body, comprising:

means for acquiring first and second volumes of 2D data sets representative of a series of rotationally offset 2D images of substantially the same selected volume in the body, the first and second data sets being acquired at different times corresponding to a pre- and a post, respectively, application of a process to the body to differentially affect imaging characteristics of the selected volume;

means for determining common reference points for spatially corresponding sub-areas in each image of the series of rotationally offset 2D images in the first and second data sets;

means for comparing in a 3D spatial manner data in sub-areas of the second data set with data in corresponding sub-areas in at least two of the rotationally offset 2D images of the first data set in order to determine a new reference point in each of the sub-areas of the first data set which results in a best match of the spatial similarity of the data in a corresponding sub-area of the second data set;

means for spatially interpolating new data for sub-areas of the first data set using the new reference points determined above and the originally acquired data of the first data set, thereby generating a new first data set for the selected volume; and means for subtracting the new first data set from the second data set, thereby generating a subtraction data set representative of a series of 2D images of the selected volume in which the given portion is accentuated.

15. The apparatus of claim 14, further including a display device responsive to said subtracted data set for displaying an image thereon of said selected volume wherein said given portion is accentuated.

16. The apparatus of claim 14, wherein said means for comparing includes transformation means for determining a 3D transformation of the spatial positioning of the data in said first data set before performing said comparing.

17. The apparatus of claim 16, wherein said transformation means includes means for 3D translation, 2D rotation, and 2D scaling in discreet fractional steps of the spatial positioning of the data in said first data set.

18. The apparatus of claim 14, wherein said acquiring means comprises a rotating x-ray source for exposing said selected volume to x-ray beams at a series of rotationally different angular positions before and after injection of an x-ray contrast agent into blood vessels of said body, and detector and measurement means for determining respective first and second data sets of intensity values representative of a series of 2D images at sequentially different angular positions of said selected volume.

* * * * *